(12) United States Patent
Busch et al.

(10) Patent No.: US 10,815,193 B2
(45) Date of Patent: Oct. 27, 2020

(54) PROCESS FOR PROVIDING HYDROGEN CHLORIDE FOR CHEMICAL REACTIONS

(71) Applicant: Covestro Deutschland AG, Leverkusen (DE)

(72) Inventors: Jan Busch, Düsseldorf (DE); Jürgen Arras, Itzehoe (DE); Christian Steffens, Cologne (DE)

(73) Assignee: Covestro Deutschland AG, Leverkusen (DE)

(*) Notice: Subject to any disclaimer, the term of this patent is extended or adjusted under 35 U.S.C. 154(b) by 218 days.

(21) Appl. No.: 15/736,427

(22) PCT Filed: Jun. 27, 2016

(86) PCT No.: PCT/EP2016/064808
§ 371 (c)(1),
(2) Date: Dec. 14, 2017

(87) PCT Pub. No.: WO2017/001320
PCT Pub. Date: Jan. 5, 2017

(65) Prior Publication Data
US 2018/0186729 A1    Jul. 5, 2018

(30) Foreign Application Priority Data
Jun. 29, 2015  (EP) .................... 15174249

(51) Int. Cl.
*C07C 263/10* (2006.01)
*C01B 7/07* (2006.01)
(Continued)

(52) U.S. Cl.
CPC .......... *C07C 263/10* (2013.01); *B01D 5/0003* (2013.01); *B01D 5/006* (2013.01);
(Continued)

(58) Field of Classification Search
CPC ..... C07C 263/10; C07C 265/14; C07C 17/02; B01D 3/14; B01D 5/0003; B01D 5/006;
(Continued)

(56) References Cited

U.S. PATENT DOCUMENTS 3,544,611 A    12/1970  Michelet et al.
3,947,484 A     3/1976  Mitrowsky et al.
(Continued)

FOREIGN PATENT DOCUMENTS

DE    844 896 C    9/1952
DE    1175666 B    8/1964
(Continued)

OTHER PUBLICATIONS

Plocker, U. et al., Process Analysis and Synthesis: Modeling, Simulation and Optimization, Ch. 9, Chemical Engineering, vol. 2, 5th ed., pp. 270-279, 2004 (English Translation Attached).
(Continued)

*Primary Examiner* — Ngoc-Yen Nguyen
(74) *Attorney, Agent, or Firm* — Donald R. Palladino (57) ABSTRACT

The invention relates to an improved process for making available the coproduct hydrogen chloride obtained in the preparation of an isocyanate by phosgenation of the corresponding amine for a desired subsequent use (i.e. a chemical reaction), in which part of the total hydrogen chloride obtained is isolated in gaseous form at a pressure which is higher than the pressure desired for the subsequent use of the hydrogen chloride by lowering the pressure of the crude product from the phosgenation and the remaining part of the total hydrogen chloride obtained is separated off at a pressure lower than that desired for the subsequent use from the liquid crude product from the phosgenation remaining after lowering of the pressure and is subsequently compressed to a pressure which is higher than that desired for the subse-
(Continued)

quent use, and in which the two hydrogen chloride streams obtained in this way are, preferably together after having been combined, purified so as to give a purified hydrogen chloride at a pressure which is higher than the pressure desired for the subsequent use.

14 Claims, 1 Drawing Sheet (51) Int. Cl.
*C01B 7/04* (2006.01)
*C07C 17/02* (2006.01)
*B01D 5/00* (2006.01)
*B01D 3/14* (2006.01)
*B01L 3/14* (2006.01)

(52) U.S. Cl.
CPC ............... *B01L 3/14* (2013.01); *C01B 7/04* (2013.01); *C01B 7/07* (2013.01); *C01B 7/0712* (2013.01); *C01B 7/0737* (2013.01); *C07C 17/02* (2013.01); *C01P 2006/80* (2013.01)

(58) Field of Classification Search
CPC ........... C01B 7/04; C01B 7/07; C01B 7/0712; C01B 7/0737
See application file for complete search history.

(56) References Cited

U.S. PATENT DOCUMENTS

| | | | |
|---|---|---|---|
| 4,289,732 A | 9/1981 | Bauer et al. | |
| 4,419,295 A | 12/1983 | Hennig et al. | |
| 5,017,979 A * | 5/1991 | Fujii | H01L 27/115 257/319 |
| 5,117,048 A | 5/1992 | Zaby et al. | |
| 6,719,957 B2 | 4/2004 | Brady et al. | |
| 6,833,469 B2 | 12/2004 | Woelfert et al. | |
| 6,916,953 B2 | 7/2005 | Walsdorff et al. | |
| 7,504,533 B2 | 3/2009 | Bohm et al. | |
| 7,584,629 B2 | 9/2009 | Sohn et al. | |
| 7,592,479 B2 | 9/2009 | Strofer et al. | |
| 7,645,900 B2 | 1/2010 | Lorenz et al. | |
| 7,819,949 B2 | 10/2010 | Sesing et al. | |
| 7,851,648 B2 | 12/2010 | Sohn et al. | |
| 8,079,752 B2 | 12/2011 | Rausch et al. | |
| 8,097,751 B2 | 1/2012 | Koch et al. | |
| 8,288,584 B2 | 10/2012 | Knoesche et al. | |
| 8,563,768 B2 | 10/2013 | Bruns et al. | |
| 9,533,885 B2 | 1/2017 | Mouazer et al. | |
| 2007/0232827 A1 | 10/2007 | Wolfert et al. | |
| 2007/0261437 A1 | 11/2007 | Boonstra et al. | |
| 2011/0236296 A1 * | 9/2011 | Shimizu | B01D 3/14 423/488 |
| 2015/0343414 A1 * | 12/2015 | Weber | C01B 7/04 423/488 |

FOREIGN PATENT DOCUMENTS

| | | |
|---|---|---|
| DE | 20 58 032 A | 5/1972 |
| DE | 300168 A7 | 5/1992 |
| FR | 69428 E | 11/1958 |
| FR | 2325637 A1 | 4/1977 |
| GB | 901377 A | 7/1962 |
| GB | 1077031 | 7/1967 |
| GB | 1173890 A | 12/1969 |
| GB | 1238669 | 7/1971 |
| GB | 1341311 | 12/1973 |
| WO | 2009059903 A1 | 5/2009 |
| WO | 2017001322 A1 | 1/2017 |

OTHER PUBLICATIONS

Ullmann's Encyclopedia of Industrial Chemistry, 4th Ed., 13: 351-353, 1977 (English Translation Attached).
Yen, Yen-Chen, Isocyanates Part 1, Supplement C, SRI International Report No. 1C, Jul. 1979.
Dubbel, Handbook of Mechanical Engineering, Springer, N11-N14, 2001 (English Translation Attached).
Ullmann's Encyclopedia of Industrial Chemistry, Wiley-VCH Verlag GmbH & Co. KGaA, Ch. 10.2.1, 597-599, 2012 (English Translation Attached).
Ullmann's Encyclopedia of Industrial Chemistry, Wiley-VCH Verlag GmbH & Co. KGaA, Ch, 1.3m 12-17, 2014 (English Translation Attached).

* cited by examiner

PROCESS FOR PROVIDING HYDROGEN CHLORIDE FOR CHEMICAL REACTIONS

CROSS-REFERENCE TO RELATED APPLICATIONS

This application is a national stage application under 35 U.S.C. § 371 of PCT/EP2016/064808, filed Jun. 27, 2016, which claims the benefit of European Application No. 15174249.1, filed Jun. 29, 2015, both of which are being incorporated by reference herein.

FIELD

The invention relates to an improved process for making available the coproduct hydrogen chloride obtained in the preparation of an isocyanate by phosgenation of the corresponding amine for a desired subsequent use (i.e. a chemical reaction), in which part of the total hydrogen chloride obtained is isolated in gaseous form at a pressure which is higher than the pressure desired for the subsequent use of the hydrogen chloride by lowering the pressure of the crude product from the phosgenation and the remaining part of the total hydrogen chloride obtained is separated off at a pressure lower than that desired for the subsequent use from the liquid crude product from the phosgenation remaining after lowering of the pressure and is subsequently compressed to a pressure which is higher than that desired for the subsequent use, and in which the two hydrogen chloride streams obtained in this way are, preferably together after having been combined, purified so as to give a purified hydrogen chloride at a pressure which is higher than the pressure desired for the subsequent use.

BACKGROUND

Many processes are known and described in the literature for producing isocyanates by phosgenation of the corresponding amines. Depending on the type of amines, the reaction can be carried out in the gas or liquid phase, either batchwise or continuously (W. Siefken, Liebigs Ann. 562, 75-106 (1949)).

The carrying out of continuous syntheses of organic isocyanates on an industrial scale has been described a number of times, see, for example, Ullmanns Encyklopädie der technischen Chemie, 4th edition (1977), volume 13, pp. 351 to 353. Here, both aromatic isocyanates such as methylenedi(phenyl isocyanate) (hereinafter MMDI—"monomeric MDI"), polymethylenepolyphenylene polyisocyanate (a mixture of MMDI and higher homologues, hereinafter PMDI, "polymeric MDI") or tolylene diisocyanate (hereinafter TDI) and also aliphatic isocyanates such as hexamethylene diisocyanate (hereinafter HDI) or isophorone diisocyanate (hereinafter IPDI) are used worldwide.

The industrial processes for production of aromatic isocyanates such as MMDI, PMDI and TDI and also aliphatic isocyanates such as HDI and IPDI are operated virtually exclusively in the continuous mode. As an example of such a process in various continuously operated vessels, mention may be made of DE-A-844 896.

The phosgenation of primary amines ($RNH_2$) is usually carried out in stages, with the carbamoyl chloride (RN-HCOCl) firstly being formed from the starting materials at low temperature and this subsequently being converted at elevated temperature into the corresponding isocyanate (RNCO), with hydrogen chloride being eliminated in both steps. During the first stage, known as the "cold phosgenation", the amine hydrochloride ("$RNH_2.HCl$"=$RNH_3Cl$) corresponding to the amine used occurs as significant by-product, and this reacts in the presence of phosgene in the "hot phosgenation" to form the corresponding isocyanate. Temperatures below 60° C. are usually employed in the cold phosgenation, while temperatures in the range from 100° C. to 200° C. are reached in the hot phosgenation. Two-stage processes are explained, for example, in the documents DE-A-20 58 032, DE-A-21 53 268 and DE-A-1 233 854.

In the preparation of an isocyanate by phosgenation of the corresponding amine, considerable amounts of hydrogen chloride are formed, corresponding to the stoichiometry of the underlying chemical reaction. In industrial processes, the major part of the hydrogen chloride is usually isolated in gaseous form from the crude product from the reaction by lowering the pressure and subsequently purified by very low temperature treatment ("freezing-out" of impurities such as phosgene). The residual liquid crude product remaining after lowering of the pressure is freed of phosgene, for example by distillation, to give a gaseous mixture of phosgene and the remaining hydrogen chloride together with a liquid mixture of isocyanate (and generally solvent). Phosgene is separated off from the gaseous mixture, for example by absorption, as a result of which the remaining hydrogen chloride is obtained in gaseous form and can subsequently be combined with the main amount of hydrogen chloride. The fundamentals of this way of carrying out the process are described in SRI International, Report No. 1C, ISOCYANATES PART I, SUPPLEMENT C, Yen-Chen Yen, July 1979. In many processes, hydrogen chloride obtained in this way leaves the process at a pressure which is lower than that desired for subsequent uses and also always still contains various impurities such as residues of phosgene, solvents, organic by-products and inert gases which can sometimes be injurious for subsequent uses.

In order for a process for preparing isocyanates on an industrial scale to be able to be operated economically, it is absolutely necessary to pass the hydrogen chloride obtained to an economically purposeful use. This can, according to the prior art, occur in various ways; the most important are the production of hydrochloric acid (typically having a concentration of above 30%) by absorption in water and the catalytic oxidation of the hydrogen chloride by means of oxygen to form chlorine (known as the Deacon process). In the first case, the hydrochloric acid can either be passed directly to a suitable use or be oxidized electrolytically to give chlorine. Chlorine obtained from the coproduct hydrogen chloride from isocyanate production can (regardless of whether it has been obtained by catalytic oxidation of the hydrogen chloride or electrolysis of hydrochloric acid prepared beforehand from the hydrogen chloride) be reacted with carbon monoxide to form phosgene, one of the starting materials for isocyanate production, so that it is possible to operate isocyanate production with an essentially closed chlorine circuit. However, it is also possible to pass the hydrogen chloride obtained to a use outside isocyanate production. For example, mention may be made of the use of chlorine obtained from the hydrogen chloride for preparing ethylene dichloride (1,2-dichloroethane, hereinafter EDC), an important starting material for, for example, the preparation of polyvinyl chloride and ethylenediamine.

Depending on the desired further use of the hydrogen chloride, the purity and pressure of the hydrogen chloride have to meet different requirements. The absorption by means of water to produce hydrochloride acid is comparatively undemanding in respect of the pressure and the purity. On the other hand, hydrogen chloride which is to be used in a Deacon process has to have a high purity in respect of organic impurities and an elevated pressure of up to 25 bar (absolute). Processes for preparing EDC require an admission pressure of the hydrogen chloride of up to 15 bar (absolute) and are likewise demanding in terms of the purity of the hydrogen chloride.

Since, as mentioned above, the hydrogen chloride is obtained in many isocyanate production processes at a pressure which is lower than that sought for many subsequent uses, the hydrogen chloride therefore has to be not only purified but also compressed for the majority of the subsequent uses. This is associated with an increased outlay in terms of apparatus and energy. However, there are also isocyanate production processes in which at least part of the hydrogen chloride, depending on the embodiment the total hydrogen chloride, is obtained at a significantly higher pressure. Thus, EP 1 616 857 A1 describes a process in which the crude product of the reaction is obtained at a pressure of up to 15 bar, and it is thus also possible to isolate the hydrogen chloride at a relatively high pressure, so that at least the process step of compression of the hydrogen chloride could in principle be dispensed with. Further examples of processes in which it is possible in principle to isolate the hydrogen chloride formed as coproduct at an elevated pressure sufficient for subsequent uses are described in the as yet unpublished European patent application No. EP15174217.8. Even if the hydrogen chloride does not have to be extremely pure in respect of organic impurities for all subsequent uses, it nevertheless has to be freed as far as possible of excess phosgene in any case.

The separation of phosgene and hydrogen chloride and residues of solvent, isocyanate, further organic compounds, inert gases, etc., present therein from the crude product from the phosgenation and the subsequent isolation of hydrogen chloride and recirculation of phosgene are described in many documents (e.g. EP1849767B1, EP1575906B1, WO2009/059903A1, WO2005/115974A1, EP1575904B1, U.S. Pat. No. 7,592,479B2, DE2252068, EP2093215A1, EP1401802B1, EP1529033B1, EP2200976B1, WO2011/003532A1, WO2009/037179A1, WO2013/026591A1).

In EP 1 849 767 B1, the separation of phosgene and hydrogen chloride is achieved in a falling film absorber. The absorber preferably operates at from 1 to 35 bar, particularly preferably from 1.2 to 3 bar. The purpose of the falling film absorber is primarily to produce a very pure hydrogen chloride gas (at the top) which is passed to further processing or to chlorine recovery. The advantage of a falling film absorber is that the phosgene is absorbed in the solvent introduced and can therefore be separated off without the hydrogen chloride itself having to be used as runback and thus condensed. Disadvantages of the use of a falling film absorber are the comparatively high costs of the apparatus and the purity of the hydrogen chloride which is insufficient for many uses.

EP 2 021 275 B1 describes the further purification by distillation of a hydrogen chloride stream as is obtained, for example, from the abovementioned falling film absorber. The gas is compressed to a pressure in the range from 5 to 30 bar, partially condensed and fractionated in a distillation column. High-purity hydrogen chloride is isolated at the top, while residues of phosgene, solvent, organics, etc., are taken off at the bottom. Energy integration minimizes the cooling energy used. Advantages of the process are the high purity of the hydrogen chloride and the low energy consumption for the distillation. A disadvantage is that the entire gas stream to be purified has to be compressed with a corresponding energy consumption. The process claimed also has the economic disadvantage that bottom streams obtained have to be disposed of as residue.

EP 1 575 906 B1 describes the separation of hydrogen chloride and phosgene at a preferred pressure of from 3 to 16 bar. Here, the gas mixture is firstly partially condensed and then distilled or stripped, with the bottom product containing hardly any hydrogen chloride. The overhead product is fed to a scrubber in order to remove remaining phosgene from the hydrogen chloride. The hydrogen chloride obtained in this way can then be compressed and fed to a Deacon or EDC process. Disadvantages are the number of process steps and thus apparatus items and also the necessity of compressing the entire hydrogen chloride.

U.S. Pat. No. 6,719,957 B2 describes a process for freeing a gas of impurities having a boiling point above 100° C. It comprises compression of the gas from 1-5 bar to 8-20 bar and a subsequent two-stage condensation to remove impurities. Energy integration between the two stages is realized here. A disadvantage of the process is the fact that phosgene and other components having boiling points below 100° C. are not separated off.

WO 2009/059903 A1 describes the separation of reaction product, phosgene and hydrogen chloride by distillation at pressures of from 3 through 10 to 30 bar. The reaction product is taken off in liquid form at the bottom of the column, phosgene is likewise taken off in liquid form at a side offtake, and hydrogen chloride is taken off in gaseous form at the top. Since the runback to the column produced by condensers should consist of phosgene and hydrogen chloride, the hydrogen chloride leaving the column still contains appreciable amounts of phosgene. Another disadvantage of low operating pressures below the hydrogen chloride output pressure required for a subsequent use is that further compression of the entire hydrogen chloride stream is necessary. At an alternatively high operating pressure, a disadvantage is that correspondingly large amounts of low-boiling solvent or phosgene are required in order to limit the temperature at the bottom of the column. This limitation of the temperature is necessary to avoid undesirable subsequent reactions (coloration, polymerization). However, the use of large amounts of solvent or phosgene means a high outlay in costs in the work-up.

DE 1593412 describes the preparation of pure hydrogen chloride as by-product of isocyanate production at above 10 atm gauge. Here, the entire free and bound hydrogen chloride is separated off in a first distillation column directly after the phosgenation. To minimize the phosgene losses, this hydrogen chloride can be freed of phosgene in a further column. A feature of the process is the complete conversion of the intermediate carbamoyl chloride, which still contains bound hydrogen chloride, into the isocyanate at the bottom of the first column, so that no hydrogen chloride has to be separated off in the further work-up of the isocyanate. A disadvantage, in turn, is that appropriately large amounts of low-boiling solvent or phosgene are required at relatively high pressure in the column in order to limit the temperature at the bottom.

WO 2005/115974 A1 describes a process for preparing isocyanates, in which the gas stream containing essentially phosgene, hydrogen chloride and solvent, which gas stream has been separated off from the reaction mixture, is fractionated in a separation unit, for example a distillation column. The purity of the recovered phosgene or hydrogen chloride and isocyanates is important to the invention. However, the purity of the hydrogen chloride is disregarded.

WO 2013/026592 describes the separation of hydrogen chloride and phosgene in a column, in which a liquid mixture containing hydrogen chloride and phosgene is introduced at the top and a gaseous mixture of the two components and optionally a stripping gas, e.g. nitrogen or carbon monoxide, is fed in at the bottom. Phosgene is scrubbed out of the hydrogen chloride in the upper part of the column, while hydrogen chloride is stripped from the phosgene in the lower part. A disadvantage is that phosgene introduced at the top will occur as impurity in the hydrogen chloride separated off at the top, and likewise nitrogen or carbon monoxide introduced.

The removal of (chloro)hydrocarbons from hydrogen chloride by means of adsorption is described in WO 2007/085627 A1, for instance in order to feed the hydrogen chloride to a Deacon process. The process aims to recover the (chloro)hydrocarbons removed in phosgene-free form. However, this means that the phosgene is not removed from the hydrogen chloride. A disadvantage is that the removal of the phosgene has to be carried out additionally before or afterwards, for example by absorption, which in turn increases the number of process steps and the costs.

In WO 2013/026591 A1, membranes are used in order to fractionate a mixture of phosgene and hydrogen chloride so as to obtain a stream rich in phosgene and low in hydrogen chloride and a stream rich in hydrogen chloride and low in phosgene. Disadvantages are the relatively high procurement and operating costs for membrane separation units.

In summary, it can be said that although the above-described processes of the prior art generally can be operated reliably, they are not free of disadvantages. The provision of the coproduct hydrogen chloride formed in isocyanate production for subsequent uses, in particular subsequent uses which set down particular demands in respect of the desired hydrogen chloride pressure and/or the desired hydrogen chloride purity, is associated with a relatively high outlay in terms of apparatus and process engineering, so that there is a need for improvement here.

SUMMARY

In the light of what has been said above, it is an object of the present invention to provide a process for making hydrogen chloride obtained as coproduct in the preparation of an isocyanate by phosgenation of the corresponding amine (10), optionally in the presence of a solvent (30), available for a desired subsequent use (i.e. for a chemical reaction) at a desired admission pressure of the hydrogen chloride (100) to be used there of $p_F$, which comprises the steps:

(i) single-stage or multistage depressurization of the crude product from the phosgenation (40), which is under the pressure $p_R$, to a pressure $p_E \geq p_F$, giving a gaseous stream (60) containing predominantly hydrogen chloride and a liquid stream (50) containing predominantly isocyanate and phosgene and also optionally solvent;

(ii) separation of phosgene from the stream (50) containing predominantly isocyanate and phosgene and also optionally solvent at a pressure $p_A < p_F$, giving a gaseous stream (80) comprising phosgene and hydrogen chloride and also optionally a subordinate amount of the solvent and a stream (70) containing isocyanate and optionally the major part of the solvent;

(iii) compression of the stream (80) containing phosgene and hydrogen chloride and also optionally a subordinate amount of the solvent to a pressure $p_V > p_F$, giving a compressed gas stream (90);

(iv) purification, preferably in a distillation column, of the stream (60) containing hydrogen chloride and of the compressed stream (90) containing phosgene and hydrogen chloride and also optionally a subordinate amount of the solvent (30), preferably after the two streams have been combined, at a pressure $p_D > p_F$, giving purified hydrogen chloride gas (100) and phosgene-containing liquid (110).

DETAILED DESCRIPTION

The process of the invention is particularly suitable for use in the preparation of methylenedi(phenyl isocyanate) (MMDI) as pure isomers or as an isomer mixture, polymethylenepolyphenyl polyisocyanate (PMDI higher homologues of MMDI having three or more benzene rings), mixtures of methylenedi(phenyl isocyanate) and polymethylenepolyphenyl polyisocyanate, tolylene diisocyanate (TDI) as pure isomers or isomer mixture, isomers of xylylene diisocyanate (XDI), isomers of diisocyanatobenzene, 2,6-xylene isocyanate, naphthylene 1,5-diisocyanate (1,5-NDI), diisocyanates based on aliphatic or cycloaliphatic hydrocarbons having from 2 to 18 carbon atoms, e.g. butane 1,4-diisocyanate, pentane 1,5-diisocyanate, hexane 1,6-diisocyanate (HDI), octane 1,8-diisocyanate, nonane 1,9-diisocyanate, decane 1,10-diisocyanate, 2,2-dimethylpentane 1,5-diisocyanate, 2-methylpentane 1,5-diisocyanate (MPDI), 2,4,4(or 2,2,4)-trimethylhexane 1,6-diisocyanate (TMDI), cyclohexane 1,3- and 1,4-diisocyanate, 1-isocyanato-3,3,5-trimethyl-5-isocyanatomethylcyclohexane (IPDI), 2,4- or 2,6-diisocyanato-1-methylcyclohexane (H6-TDI), 1-isocyanato-1-methyl-4(3)-isocyanatomethylcyclohexane (AMCI), 1,3(and/or 1,4)-bis(isocyanatomethyl)cyclohexane, bis(isocyanatomethyl)norbornane (NBDI), 4,4' (and/or 2,4')-diisocyanatodicyclohexylmethane, and (cyclo) aliphatic triisocyanates having up to 22 carbon atoms, e.g. triisocyanatocyclohexane, tris(isocyanatomethyl)cyclohexane, triisocyanatomethylcyclohexane, 1,8-diisocyanato-4-(isocyanatomethyl)octane, undecane 1,6,11-triisocyanate, 1,7-diisocyanato-4-(3-isocyanatopropyl)heptane, 1,6-diisocyanato-3-(isocyanatomethyl)hexane or 1,3,5-tris(isocyanatomethyl)cyclohexane. The process of the invention is very particularly preferably suitable for use in the preparation of tolylene diisocyanate, diphenylmethane diisocyanate and polyphenylenepolymethylene polyisocyanate.

The amines corresponding to the above polyisocyanates are aromatic polyamines such as methylenedi(phenylamine) (MMDA) as pure isomers or as isomer mixture, polymethylenepolyphenyl polyamine (PMDA), mixtures of methylenedi(phenylamine) and polymethylenepolyphenyl polyamine, toluenediamine (TDA) as pure isomers or isomer mixture, isomers of xylylenediamine (XDA), isomers of diaminobenzene, 2,6-xylidine, 1,5-naphthylenediamine (1,5-NDA), polyamines based on aliphatic or cycloaliphatic hydrocarbons having from 2 to 18 carbon atoms, e.g. 1,4-diaminobutane, 1,5-diaminopentane, 1,6-diaminohexane (HDA), 1,8-diaminooctane, 1,9-diaminononane, 1,10-diaminodecane, 2,2-dimethyl-1,5-diaminopentane, 2-methyl-1,5-pentanediamine (MPDA), 2,4,4(or 2,2,4)-trimethyl-1,6-diaminohexane (TMDA), 1,3- and 1,4-diaminocyclohexane, 1-amino-3,3,5-trimethyl-5-aminomethylcyclohexane (IPDA), 2,4- or 2,6-diamino-1-methylcyclohexane (H6-TDA), 1-amino-1-methyl-4 (3)-aminomethylcyclohexane (AMCA), 1,3 (and/or 1,4)-bis(aminomethyl)cyclohexane, bis(aminomethyl)norbornane (NBDA), 4,4'(and/or 2,4)-diaminodicyclohexylmethane, (cyclo)aliphatic polyamines having up to 22 carbon atoms, e.g. triaminocyclohexane, tris(aminomethyl)cyclohexane, triaminomethylcyclohexane, 1,8-di amino-4-(aminomethyl)octane, 1,6,11-undecanetriamine, 1,7-diamino-4-(3-aminopropyl)heptane, 1,6-diamino-3-(aminomethyl)hexane or 1,3,5-tris(aminomethyl)cyclohexane.

The process of the invention is particularly suitable for use in the preparation of methylenedi(phenyl isocyanate) (MMDI) as pure isomers or as isomer mixture, polymethylenepolyphenyl polyisocyanate (PMDI), mixtures of methylenedi(phenyl isocyanate) and polymethylenepolyphenyl polyisocyanate, tolylene diisocyanate (TDI) as pure isomers or isomer mixtures, isomers of xylylene diisocyanate (XDI), isomers of diisocyanatobenzene, 2,6-xylene isocyanate, naphthylene 1,5-diisocyanate (1,5-NDI).

Particular preference is given to using the process of the invention in the preparation of diphenylmethane diisocyanate (MMDI) and/or polyphenylenepolymethylene polyisocyanate (PMDI). For the purposes of the present invention, MMDI and PMDI are also referred to collectively as MDI, regardless of the degree of polymerization and isomer distribution; an analogous situation applies to MDA.

The preparation of the corresponding polyamines is adequately known from the prior art and will therefore not be described in detail at this point. In the case of the particularly preferred polyisocyanate MDI, the corresponding polyamine MDA is obtained by acid-catalyzed condensation of aniline and formaldehyde. This gives a mixture of the "two-ring compound" MMDA (containing two benzene rings each bearing an amino group) and higher homologues PMDA ("multiring compounds" containing three or more benzene rings each bearing an amino group). In most industrially practiced processes, this mixture is phosgenated without prior separation into monomeric and polymeric constituents. Separation into monomeric constituents and polymeric constituents therefore usually takes place only at the stage of the polyisocyanate. Here, the two-ring compound (MMDI) and secondly a mixture of the two-ring compound (MMDI) and the higher homologues (PMDI) are obtained.

Embodiments of the invention will be described in more detail below. Here, various embodiments can be combined with one another in any way as long as the contrary is not indicated to a person skilled in the art from the context.

Figure 1:
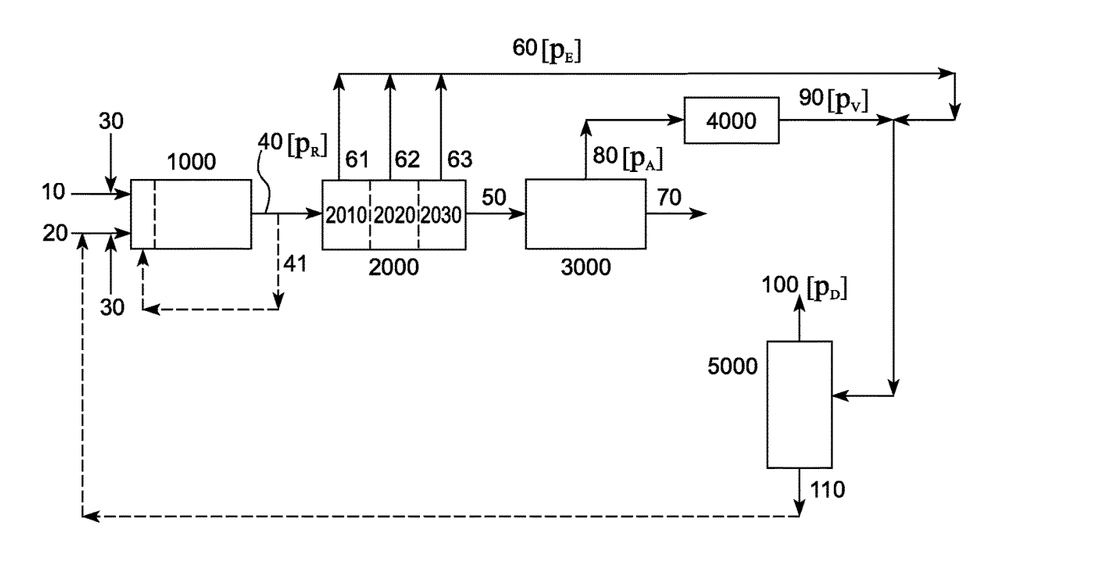
FIG. 1 is a flowchart of an embodiment of the process of the invention in which the phosgenation reaction is also shown.

A possible embodiment of the process of the invention in which the phosgenation reaction is also shown is depicted in FIG. 1:

Amine (10) and phosgene (20) are dissolved in a solvent (30) which is inert under the reaction conditions, preferably in such a way that the resulting phosgene-containing stream has a proportion by mass of from 5% to 95%, preferably from 20% to 75%, particularly preferably from 30% to 60%, of phosgene and a proportion by mass of from 95% to 5%, preferably from 80% to 25%, particularly preferably from 70% to 40%, of an inert solvent, in each case based on the total mass of the phosgene-containing stream, the amine-containing stream has a proportion by mass of from 5% to 95%, preferably from 10% to 60%, particularly preferably from 30% to 45%, of amine and a proportion by mass of from 95% to 5%, preferably from 90% to 40%, particularly preferably from 75% to 55%, of an inert solvent, in each case based on the total mass of the amine-containing stream.

Here, inert under the reaction conditions means that the solvent does not react to a significant extent with the starting materials, intermediates and end products of the reaction. The inert solvent (30) for stream (10) and stream (20) is therefore preferably selected independently from among chlorobenzene, dichlorobenzene, toluene, dioxane, dimethyl sulphoxide and mixtures of two or more of the abovementioned solvents. Chlorobenzene and dichlorobenzene are particularly preferred for both streams (10) and (20), with very particular preference being given to chlorobenzene. In the case of dichlorobenzene, the ortho isomer (ortho-dichlorobenzene) is particularly preferred.

The amine- and phosgene-containing streams obtained in this way are mixed (not shown in FIG. 1) and reacted in a reactor (1000), where the mixing apparatus used can also be integrated into the reactor (1000). Any mixing apparatus known from the prior art can be used here. Examples which may be mentioned are static mixers, in particular nozzles such as annular slit nozzles (DE-A-1792660), ring-hole nozzles (DE-C1-3744001), flat jet mixing nozzles (EP-A1-0 065 727), fan jet nozzles (DE-A1-2950216), angular jet chamber nozzles (DD-A7-300.168), three-fluid nozzles (DD-A1-132340), countercurrent mixing chambers (DE-B1146872), banking-up nozzles (FR-E-69428) and Venturi mixing nozzles (DE-B1175666). Dynamic mixers, in particular rotor-stator or turbine-like systems in which the reactants are introduced in concurrent into the mixing unit are also suitable. The mixer described in EP-A-2 077 150 may be mentioned as an example.

The reaction in the reactor (1000) gives a crude product (40) comprising isocyanate, solvent, hydrogen chloride, unreacted phosgene and, depending on the precise reaction conditions, proportions of carbamoyl chloride and possibly relatively small amounts of amine hydrochloride. The only prerequisite for carrying out the process of the invention is that this crude product is obtained at a pressure $p_R$ which is greater than the pressure $p_F$ desired for the subsequent use of the hydrogen chloride, and indeed at least so much greater that the gas stream (60) which is obtained in step (i) (see below for details) and, in contrast to the gas stream (80) obtained in step (ii), is not compressed further has a pressure level which allows a sufficient gas flow via the purification apparatus (5000) used in step (iv) to the subsequent use. As long as this prerequisite is satisfied, the reaction in the reactor (1000) can be carried out by any known method of the prior art. $p_R$ is preferably from 6.00 bar to 60.0 bar, particularly preferably from 12.0 bar to 45.0 bar. The crude product (40) preferably has a temperature $T_R$ in the range from 80° C. to 200° C., preferably from 110° C. to 170° C.

Thus, any phosgenation reactor known from the prior art can in principle be used as reactor (1000). Preference is given to using upright tube reactors through which flow occurs from the bottom. To narrow the residence time, the tube reactor can be segmented by means of suitable internals known to those skilled in the art. The present invention also encompasses embodiments in which a plurality of reactors (1000) are connected in series or in parallel.

In one embodiment of the process of the invention, the reactor (1000) is operated adiabatically, i.e. without deliberate introduction or removal of heat. In such a process, the enthalpy of reaction is, disregarding unavoidable heat losses, reflected quantitatively in the temperature difference between outlet stream and inlet stream. To avoid heat losses, the reactor is preferably insulated. The document EP 1 616

857 A1 describes the adiabatic mode of operation of polyamine phosgenation in detail, especially in paragraphs [0014] to [0018].

In another embodiment of the process of the invention, the reactor (1000) is operated isothermally, i.e. with introduction of heat via a thermostatable reactor by means of a suitable heat transfer medium (e.g. heat transfer oil, salt melt). The documents DE 1768439 A1, in particular paragraph [0003] on page 8 and EP 1 616 857 B1, in particular paragraphs [0021] to [0022], may be mentioned by way of example for the phosgenation of polyamines using an isothermal mode of operation.

It is also possible (not shown in FIG. 1) to use a sequence of a plurality of reactors (1000) which can independently be operated isothermally or adiabatically. Preference is given to a sequence of two reactors connected in series, of which the first is operated adiabatically and the second is operated isothermally, as described in EP 1 616 857 A1.

Furthermore, it is possible to branch off a substream (41) from the crude product (40) and recirculate this to the mixing of amine- and phosgene-containing stream ("reaction circuit"; shown by means of a broken line in FIG. 1). Such a process is described in the as yet unpublished European patent application No. EP15174217.8.

The crude product (40) obtained under the pressure $p_R$ is separated by depressurization, i.e. with lowering of the pressure to a pressure $p_E > p_F$, into a liquid phase (50) containing predominantly isocyanate and phosgene and also solvent (30) and a gaseous phase (60) containing predominantly hydrogen chloride and subordinate proportions of phosgene in a separator (2000) (step (i)). The separator (2000) can also be configured as a cascade of a plurality of separators (2010, 2020, 2030, ...) connected in series with a successively decreasing pressure level, where the liquid phase obtained in one separator is fed into the following separator (naturally with the exception of the liquid phase from the last separator, which represents the stream (50) containing predominantly isocyanate and phosgene and also optionally solvent). The individual gas phases (61, 62, 63, ...) are combined to form the gas stream (60) which has a pressure $p_E$ and preferably makes up from 30% to 80%, particularly preferably from 50 to 70%, of the total hydrogen chloride obtained. Separator (2000) and reactor (1000) can also be combined in a single apparatus. It is also possible (not shown in FIG. 1) to discharge a gaseous purge stream from the reactor (1000) even during the actual reaction of amine and phosgene. Such a purge stream containing predominantly hydrogen chloride is combined with the other streams (61, 62, 63, ...) to form the gas stream (60). $p_E$ is preferably from 5.00 bar to 30.0 bar, particularly preferably from 9.00 bar to 18.0 bar. The gas stream (60) preferably has a temperature $T_E$ in the range from 90° C. to 170° C., preferably from 110° C. to 150° C.

The liquid phase (50) leaving the last separator is freed of phosgene at a pressure $p_A < p_F$ in the apparatus (3000), giving a gaseous stream (80) containing phosgene and hydrogen chloride and also a subordinate amount of the solvent and a stream (70) containing isocyanate and the major part of the solvent (step (ii)). In a preferred embodiment, the apparatus (3000) is a distillation column, hereinafter referred to as dephosgenation column. In this case, the pressure $p_A$ designates the pressure at the top of the dephosgenation column and is preferably from 0.50 bar to 5.00 bar, particularly preferably from 1.00 bar to 3.00 bar. The gaseous product (80) leaving the dephosgenation column (3000) preferably has a temperature $T_A$ in the range from 10° C. to 90° C., preferably from 30° C. to 70° C. The dephosgenation column (3000) is preferably configured as a bubble cap tray column. It is also possible for a plurality of distillation columns to be connected in series. In this case, $p_A$ designates the pressure at the top of the last distillation column.

The liquid stream (70) obtained from the dephosgenation column is freed of solvent (30) as described in the prior art and worked up further (not shown in FIG. 1).

In contrast to the prior art, the gas phase (80) obtained in the dephosgenation column (3000), which preferably comprises from 20% to 70%, particularly preferably from 30% to 50%, of the total hydrogen chloride obtained, is not fed to a further stage to separate off phosgene (e.g. by absorption in a falling film absorber) but instead is compressed without further purification to the pressure $p_V$ (stream (90)) in a compressor (4000) (step (iii)). Suitable compressors for compressing corrosive gases are known to those skilled in the art and are described, for example, in EP 2 021 275 B1. Examples which may be mentioned are turbo compressors, piston compressors, screw compressors or liquid-ring compressors. $p_V$ is preferably from 5.00 bar to 30.0 bar, particularly preferably from 9.00 bar to 18.0 bar. Stream (90) preferably has a temperature $T_V$ in the range from 90° C. to 170° C., preferably from 110° C. to 150° C. Particular preference is given to combining the stream (90) with the gas stream (60), as shown in FIG. 1. If present, the pressure difference between $p_E$ and $p_V$ should be selected so that it is negligibly small at the point at which the two streams are combined. Here, as is known to those skilled in the art, pressure drops as a result of distances to be overcome in pipes have to be taken into account, i.e. $p_E$ and $p_V$ should be selected so that sufficient flow of the corresponding gas streams to the combination point and from there to the purification apparatus (5000) is ensured. It is also conceivable for $p_E$ and $p_V$ to be identical. In the case of a pressure difference between the two pressures, this is preferably from >0.00 bar to 7.00 bar, particularly preferably from 1.00 bar to 5.00 bar.

The purification apparatus (5000) for carrying out step (iv) is preferably a distillation column. The pressure $p_D$ then corresponds to the pressure at the top of the distillation column where the gaseous stream of purified hydrogen chloride (100) is taken off. A phosgene-containing liquid phase (110) is taken off from the bottom of the distillation column and is preferably recirculated to the reaction (shown by means of a broken line in FIG. 1). The liquid phase (110) is preferably mixed with the phosgene-containing stream composed of phosgene (20) and solvent (30). $p_D$ is preferably from 1.01 bar to 22.5 bar, particularly preferably from 5.00 bar to 17.5 bar. The overhead product (100) leaving the distillation column (5000) preferably has a temperature $T_D$ in the range from 50° C. to 20° C., preferably from 30° C. to 10° C. Suitable distillation columns (5000) are known to those skilled in the art and are described, for example, in Dubbel, "Taschenbuch für den Maschinenbau", Springer, 2001, p. N 11 to N 14. It is also possible for a plurality of distillation columns to be connected in series. In this case, $p_D$ designates the pressure at the top of the last distillation column.

For the purposes of the present invention, step (iv) is preferably carried out as follows:

The streams (60) and (90) are preferably combined and the combined stream is conveyed through a heat exchanger to give a liquid stream and a gaseous stream which are both fed into the purification apparatus (5000) configured as distillation column, preferably with the gaseous stream being introduced above the liquid stream. In this heat exchanger, the stream is preferably cooled to a temperature in the range from 0° C. to 50° C., particularly preferably in the range from 10° C. to 30° C.

The gaseous stream obtained at the top of the distillation column (5000) is then conveyed through another heat exchanger in which partial liquefaction of this stream takes place as a result of indirect cooling (by means of a coolant introduced from the outside) to a temperature in the range from −50° C. to 20° C., particularly preferably in the range from 30° C. to 10° C. The liquid phase obtained in this way is recirculated to the top of the distillation column (5000). The remaining gaseous phase (the purified hydrogen chloride gas (100)) has a lower temperature than the streams (60) and (90) and is fed into the heat exchanger located downstream of the compressor (4000), in which heat exchanger it is employed for indirect cooling of the combined streams (90) and (60). As a result, the gas stream (100) is heated but its composition is not altered.

The hydrogen chloride stream (100) produced by the process of the invention has a high purity and is therefore also suitable for sensitive applications such as use in a Deacon process. Furthermore, the hydrogen chloride stream (100) is at a pressure $p_D$ which is higher than the pressure $p_F$ desired for the subsequent use. In the ideal case, the pressure difference is only so great that the pressure $p_F$ desired for the subsequent use is achieved without further measures as a result of inherent pressure decreases during transport of the hydrogen chloride (100) to the subsequent use. If this is not the case, the desired pressure $p_F$ can be set by installation of a simple pressure reducer known to those skilled in the art.

Preferred subsequent uses of the hydrogen chloride (100) are:

Catalytic oxidation by means of oxygen to chlorine ("Deacon process"), which is preferably carried out at a pressure $p_F$ of from 1.00 bar to 25.0 bar, preferably from 1.50 bar to 17.00 bar, particularly preferably from 1.5 to 17 bar and in particular from 2.0 to 15 bar (absolute). The Deacon process is known to those skilled in the art and is described, for example, in Ullmann's Encyclopedia of Industrial Chemistry, 2012 Wiley-VCH Verlag GmbH & Co. KGaA, Weinheim, chapter 10.2.1 (pp. 597 to 599), and the literature cited therein. Here, catalysts based on metal oxides and/or chlorides (in particular of the metals ruthenium, chromium, tin, cerium or mixtures of at least two of these metals) are, for the purposes of the present invention, preferred over the use of inorganic acids as catalysts.

Reaction to form ethylene dichloride (EDC) by oxychlorination of ethane or ethylene, preferably ethylene, which is preferably carried out at a pressure $p_F$ of from 1.00 bar to 15.0 bar, preferably from 4.00 bar to 12.0 bar (absolute). The EDC process is known to those skilled in the art and is described, for example, in Ullmann's Encyclopedia of Industrial Chemistry, 2014 Wiley-VCH Verlag GmbH & Co. KGaA, Weinheim, chapter 1.3 (pp. 12 to 17), and the literature cited therein.

The above-described process is also of particular economic importance for the reason that the ever increasing isocyanate production capacities make the question of how to make economically purposeful use on site of the hydrogen chloride inevitably obtained more urgently.

The invention is illustrated by the following examples.

EXAMPLES

The examples presented below are based on a process simulation of the respective steady-state operating conditions, the essentials of which are described, for example, in U. Plöeker, R. Janowsky, H. Briesen, W. Marquardt, "Prozessanalyse und-synthese: Modellierung, Simulation und Optimierung", chapter 9 "Stationäre and dynamische Prozesssimulation" in "Chemische Technik", Winnacker, Küchler (editor), volume 2, $5^{th}$ edition, Wiley-VCH-Verlag, Weinheim, 2004, pages 270-279. The numerical solution of the steady-state operating conditions according to the model was based firstly on the phase equilibria of the individual components and secondly on the reaction kinetics for the reaction of MDA with phosgene while maintain, ng the energy and mass balance.

72 t/h of a 55% strength by mass solution of phosgene in monochlorobenzene (MCB) and 95 t/h of a 42% strength by mass solution of a mixture of diamines and polyamines of the diphenylmethane series (MDA) in MCB are reacted, giving a crude product stream 40 ($p_R$). Depending on the reaction conditions in the reactor 1000 (cf. FIG. 1), this stream is under a particular pressure $p_R$. In each case, about 29.5 t/h of an HCl stream 100 containing about 1 ppm of phosgene, which satisfies the requirements of a subsequent use such as the Deacon or EDC process, are obtained after distillation and compression. The runbacks/bottom fractions of the individual process stages are recirculated to the work-up process for the isocyanate.

Example 1 (According to the Invention, $p_R$=40 Bar (Absolute))

The following table shows the results. Data for the streams are based on the designations in FIG. 1.

| Stream | 50 | 60 | 70 | 80 | 90 | 100 | 110 |
|---|---|---|---|---|---|---|---|
| Index i | — | E | — | A | V | D | — |
| HCl/kg/h | 3465.6 | 18534.5 | — | 11754.3 | 11754.3 | 29423.0 | 865.8 |
| Phosgene/kg/h | 1222.0 | 776.9 | 0.1 | 1219.0 | 1219.0 | 0.03 | 1995.9 |
| MCB/kg/h | 81974.4 | 1647.8 | 77388.0 | 668.1 | 668.1 | — | 2315.9 |
| Crude MDI[1] | 58389.9 | — | 50446.5 | — | — | — | — |
| Total/kg/h | 141586.3 | 20959.2 | 127834.6 | 13641.4 | 13641.4 | 29423.03 | 5177.6 |
| $T_i$/° C. | 114.6 | 130.6 | 189.7 | 50.0 | 131.9 | −22.6 | 9.8 |
| $p_i$/bar | 3.00 | 12.0 | 3.00 | 3.00 | 12.0 | 11.0 | 11.0 |

[1])Crude MDI consisting of MDI, carbamoyl chlorides and carbodiimides.

Example 2 (According to the Invention, $p_R$=20 Bar (Absolute))

The following table shows the results. Data for the streams are based on the designations in FIG. 1.

|  | Stream | | | | | | |
|---|---|---|---|---|---|---|---|
|  | 50 | 60 | 70 | 80 | 90 | 100 | 110 |
| Index i | — | E | — | A | V | D | — |
| HCl/kg/h | 3096.4 | 20992.7 | — | 9323.0 | 9323.0 | 29419.4 | 896.3 |
| Phosgene/kg/h | 987.5 | 963.0 | 0.1 | 1005.9 | 1005.9 | 0.03 | 1968.8 |
| MCB/kg/h | 81491.7 | 2164.2 | 75889.3 | 530.2 | 530.2 | — | 2694.4 |
| Crude MDI[1] | 56071.5 | 0.1 | 50418.4 | — | — | — | 0.1 |
| Total/kg/h | 141647.1 | 24120.0 | 126307.8 | 10859.1 | 10859.1 | 29419.5 | 5559.6 |
| $T_i$/° C. | 125.4 | 123.0 | 189.8 | 50.0 | 131.8 | −22.6 | 10.9 |
| $p_i$/bar | 3.00 | 12.0 | 3.00 | 3.00 | 12.0 | 11.0 | 11.0 |

[1]Crude MDI consisting of MDI, carbamoyl chlorides and carbodiimides.

The examples show that hydrogen chloride can successfully be obtained in the desired purity without the entire hydrogen chloride formed in the isocyanate process (i.e. the sum of hydrogen chloride in stream 60 and in stream 80) having to be compressed. In contrast, the entire hydrogen chloride stream has to be compressed in the process described in EP 2 021 275 B1. In addition, secondary components which have to be disposed of are formed.

level, where a gaseous, hydrogen chloride-containing phase is taken off from each separator and these individual gaseous phases containing hydrogen chloride are further combined to form the gaseous stream containing hydrogen chloride, the pressure of which corresponds to the pressure $p_E$.

The invention claimed is:

1. A process for making hydrogen chloride, obtained as coproduct in the preparation of an isocyanate by phosgenation of a corresponding amine, optionally in the presence of a solvent, available for a desired subsequent use at a desired admission pressure of the hydrogen chloride of $p_F$, comprising:
   (i) single-stage depressurizing or multistage depressurizing crude product from the phosgenation, which is under a pressure $p_R$, to a pressure $p_E > p_F$, thereby giving a gaseous stream containing hydrogen chloride and a liquid stream containing isocyanate and phosgene and also optionally solvent;
   (ii) separating phosgene from the liquid stream containing isocyanate and phosgene and also optionally solvent at a pressure $p_A < p_F$, thereby giving a gaseous stream comprising phosgene and hydrogen chloride and a stream containing isocyanate and optionally solvent;
   (iii) compressing the gaseous stream comprising phosgene and hydrogen chloride to a pressure $p_V > p_F$, thereby giving a compressed gas stream; and
   (iv) purifying the gaseous stream containing hydrogen chloride and the compressed gas stream at a pressure $p_D > p_F$, thereby giving purified hydrogen chloride gas and phosgene-containing liquid,
   wherein the subsequent use is selected from among:
      the preparation of chlorine by catalytic oxidation of hydrogen chloride by means of oxygen at a value of $p_F$ in the range from 1.00 bar to 25.0 bar and
      the reaction to form ethylene dichloride by oxychlorination of ethane or ethylene at a value of $p_F$ in the range from 1.00 bar to 15.0 bar.

2. The process of claim 1, wherein step (i) is carried out in a separator.

3. The process of claim 2, wherein the separator is configured as a cascade of a plurality of separators connected in series with a successively decreasing pressure 4. The process of claim 1, wherein step (ii) is carried out in a dephosgenation column.

5. The process of claim 1, wherein step (iv) is carried out in a distillation column.

6. The process of claim 5, wherein the gaseous stream containing hydrogen chloride and the compressed gas stream are combined before step (iv) is carried out.

7. The process of claim 6, wherein in step (iv):
   (1) the stream obtained by combining the gaseous stream containing hydrogen chloride and the compressed gas stream is partially condensed by indirect cooling in a heat exchanger thereby producing a resulting liquid stream and a resulting gas stream,
   (2) the resulting liquid stream and the resulting gas stream are fed into the distillation column,
   (3) a gaseous stream obtained at the top of the distillation column is partially condensed by indirect cooling in another heat exchanger,
   (4) a liquid phase obtained in (iv.3) is recirculated to the top of the distillation column, and
   (5) a gas phase obtained in the partial condensation of (3) is used as medium for indirect cooling in step (iv.1).

8. The process of claim 1, wherein the isocyanate is selected from the group consisting of methylenedi(phenyl isocyanate) as pure isomer or as isomer mixture, polymethylenepolyphenyl polyisocyanate, mixtures of methylenedi(phenyl isocyanate) and polymethylenepolyphenyl polyisocyanate, tolylene diisocyanate as pure isomer or isomer mixture, isomers of xylylene diisocyanate, isomers of diisocyanatobenzene, 2,6-xylene isocyanate and naphthylene 1,5-diisocyanate.

9. The process of claim 1, wherein
   $p_R$ has a value in the range from 6.00 bar to 60.0 bar,
   $p_E$ has a value in the range from 5.00 bar to 30.0 bar,
   $p_A$ has a value in the range from 0.50 bar to 5.00 bar,
   $p_V$ has a value in the range from 5.00 bar to 30.0 bar and
   $p_D$ has a value in the range from 1.01 bar to 25.5 bar.

10. The process of claim 1, wherein
    $p_R$ has a value in the range from 12.0 bar to 45.0 bar,
    $p_E$ has a value in the range from 9.00 bar to 18.0 bar;
    $p_A$ has a value in the range from 1.00 bar to 3.00 bar;
    $p_V$ has a value in the range from 9.00 bar to 18.0 bar and
    $p_D$ has a value in the range from 5.00 bar to 17.5 bar.

11. The process of claim 9, wherein
    the crude product from the phosgenation has a temperature $T_R$ in the range from 80° C. to 200° C., the gaseous stream containing hydrogen chloride has a temperature $T_E$ in the range from 90° C. to 170° C., the gaseous stream comprising phosgene and hydrogen chloride has a temperature $T_A$ in the range from 10° C. to 90° C., the compressed gas stream has a temperature $T_V$ in the range from 90° C. to 170° C. and the purified hydrogen chloride gas has a temperature $T_D$ in the range from −50° C. to 20° C.

12. The process according to claim 10, wherein the crude product form the phosgenation has a temperature $T_R$ in the range from 110° C. to 170° C., the gaseous stream containing hydrogen chloride has a temperature $T_E$ in the range from 110° C. to 150° C., the gaseous stream comprising phosgene and hydrogen chloride has a temperature $T_A$ in the range from 30° C. to 70° C., the compressed gas stream has a temperature $T_V$ in the range from 110° C. to 150° C. and the purified hydrogen chloride gas has a temperature $T_D$ in the range from −30° C. to −10° C.

13. The process of claim 10, wherein the subsequent use is selected from among the preparation of chlorine by catalytic oxidation of hydrogen chloride by means of oxygen at a value of $p_F$ in the range from 1.50 bar to 17.0 bar, and the reaction to form ethylene dichloride by oxychlorination of ethane or ethylene at a value of $p_F$ in the range from 4.00 bar to 12.0 bar.

14. The process of claim 12, wherein the subsequent use is selected from among the preparation of chlorine by catalytic oxidation of hydrogen chloride by means of oxygen at a value of $p_F$ in the range from 1.50 bar to 17.0 bar, and the reaction to form ethylene dichloride by oxychlorination of ethane or ethylene at a value of $p_F$ in the range from 4.00 bar to 12.0 bar.

* * * * *